United States Patent [19]

Bellm

[11] Patent Number: 4,848,334
[45] Date of Patent: Jul. 18, 1989

[54] MASK
[75] Inventor: Howard G. Bellm, Binfield, Great Britain
[73] Assignee: Lifeline Limited, Vale, Great Britain
[21] Appl. No.: 13,700
[22] Filed: Feb. 12, 1987
[30] Foreign Application Priority Data Feb. 13, 1986 [GB] United Kingdom ............... 8603558

[51] Int. Cl.$^4$ .......................................... A62B 18/08
[52] U.S. Cl. ........................ 128/207.11; 128/206.24
[58] Field of Search ................. 128/202.27, 205.11, 128/205.25, 206.12, 206.21, 206.22, 206.24, 206.12, 206.28, 207.11, 207.13, 911, 202.28–203.11, 203.19–204.12, 207.17; 24/298–302, 3 M, 16 PB, 88 PB, 265 R, 129 R, 129 W

[56] References Cited

U.S. PATENT DOCUMENTS

| | | | |
|---|---|---|---|
| 2,176,709 | 10/1939 | Dym | 128/207.11 |
| 2,477,706 | 8/1949 | Taylor | 128/207.13 |
| 2,843,121 | 7/1958 | Hudson | 128/207.11 |
| 3,170,463 | 2/1965 | Duggan | 128/207.11 |
| 3,721,239 | 3/1973 | Myers | 128/911 |
| 4,007,737 | 2/1977 | Paluch | 128/911 |
| 4,235,464 | 11/1980 | Kraus | 24/16 PB |
| 4,671,271 | 6/1987 | Bishop et al. | 128/207.11 |

FOREIGN PATENT DOCUMENTS

| | | | |
|---|---|---|---|
| 2951019 | 8/1980 | Fed. Rep. of Germany | 128/207.11 |
| 712954 | 8/1931 | France | 128/207.11 |
| 37712 | 3/1936 | Netherlands | 128/206.24 |
| 491290 | 8/1938 | United Kingdom | 128/204.26 |

Primary Examiner—Max Hindenburg
Assistant Examiner—K. M. Reichle
Attorney, Agent, or Firm—Fliesler, Dubb, Meyer & Lovejoy

[57] ABSTRACT

A mask assembly for allowing application of gases to the nose and mouth of a person, the mask assembly including a gas delivery nozzle, a mask adapted to cover the nose and mouth of the person, and a retaining strap, the gas nozzle having one end connected to the mask and a free end adapted for connection to a connector assembly, the retaining strap including a clip member and a strap, the strap being adapted to extend around the back of the head of the person and having one end connected to one side of the mask and a free end, the clip member including first and second parts, one of the parts being attached to the free end of the strap and the other one of the parts being attached to the other side of the mask, a specified one of the first and second parts having first and second longitudinally spaced opposite ends, being attached to the mask or strap, respectively, at the first end and adapted for connecting the other of the parts thereto at different selected positions along its length, so that the effective length of the strap is variable, and all parts of the mask assembly being integrally molded of the same substantially non-elastic plastics material.

8 Claims, 3 Drawing Sheets

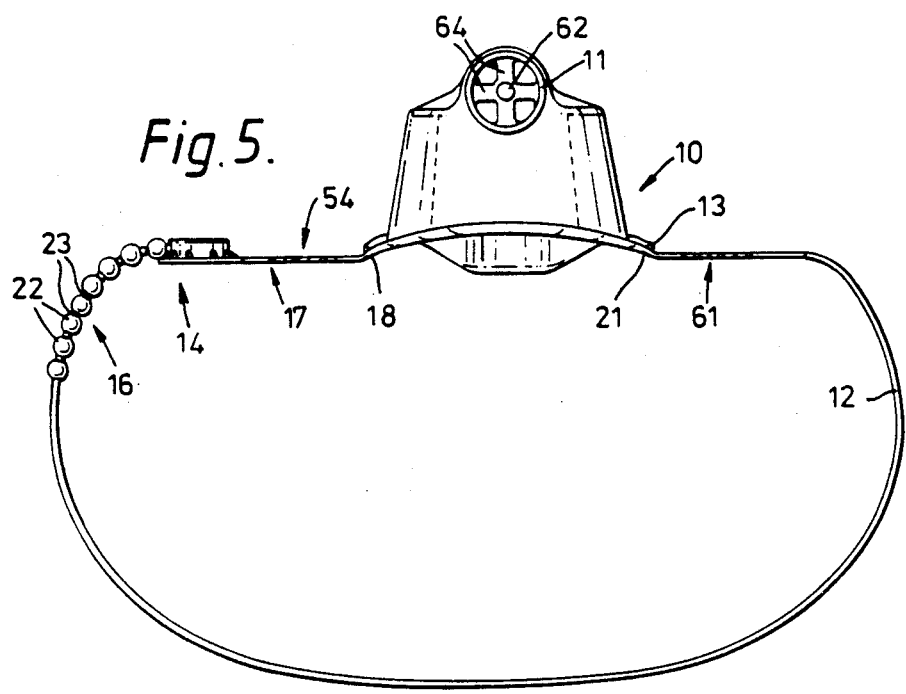
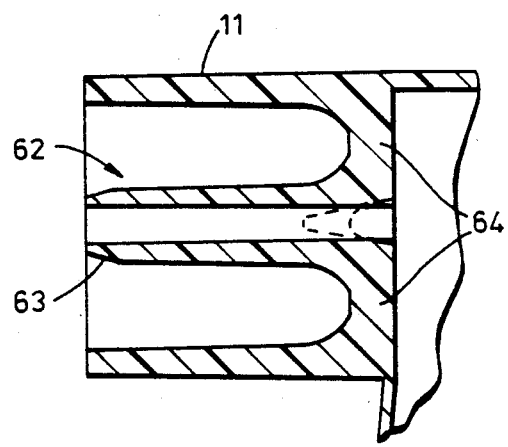
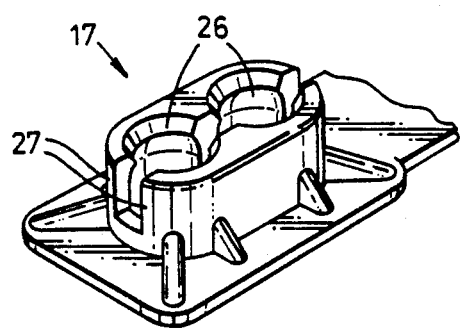

MASK

TECHNICAL FIELD

The present invention relates to a mask preferably but not exclusively for medical use for administering gases such as oxygen or for use with a nebulizer.

BACKGROUND OF THE INVENTION

Hitherto masks have been widely used in medical practice for the application of gases or, more recently, for use with nebulization, that is the application of drugs to a pateint by means of an aerosol produced by a flow of gas, the aerosol and drug being breathed in through a face mask.

For hygienic reasons, it is preferred to use a new mask for each treatment. Thus masks have increasingly become considered to be disposable items. Hitherto, however, mask assemblies have comprised a face mask of generally plastics material, a separately formed nozzle for connecting to the supply of gas, and a retaining strap generally in the form of a separate woven elastic strap connected to the mask itself by various means including knots in the woven elastic and holes in the mask. Various configurations of face mask have been tried but they suffer from the disadvantage of being relatively costly items, and in particular generally being more costly than is desirable in a disposable item.

In particular the cost of the mask is increased because the strap for holding the mask in contact with the face is a separately produced item and manual labour is required to assemble the strap and the mask whether the strap is connected to the mask simply by passing the strap through the hole in the mask and tying a knot there behind or by other clip means which typically comprise metal rings. An example of such a mask is disclosed in British Patent Specification No. 920216 in which the mask is retained to the patients face by means of tapes or elastic bands 15 which are attached at spaced points to the periphery of the mask and are then passed around the back of the patient's head. The mask in British Specification No. 920216 is intended to cover the nose and mouth of the patient and includes a gas delivery pipe 11 in addition to the tapes 15. It will be understood that the mask comprises a number of other separate parts, the gas delivery pipe 11, the collar 19, the wire 14 and the skirt portion 21.

The applicants have also had drawn to their attention French Specification No. 8482268 which shows a gas mask moulded in a resilient material (rubber). There are considerable difficulties in moulding rubber at high speed which is necessary if the mask is to be produced cheaply. Furthermore, the moulding arrangement disclosed in the French Specification No. 848268 would not lend itself to moulding with a suitable modern plastics material. If a resilient elastic material such as rubber is used for a mask, then because of its resiliency it has to be of substantial thickness to be self supporting and able to maintain its shape. In particular, the cup shape part covering the nose and mouth must be fairly thick to be sufficiently rigid to maintain its shape when the patient breathes in. This is very wasteful of material and makes the mask very expensive. For this reason, a more rigid plastics material must be used which will maintain its shape. Such a material is substantially non-elastic and it is therefore not possible to mould it in the way shown in the French patent specification. It is only by the use of such a material that a sufficiently rigid mask can be made which is of thin-wall section elastic. Furthermore, the mask in the French specification is incomplete requiring the addition of glass or other material for the eye holes.

SUMMARY OF THE INVENTION

The present invention provides a mask assembly for allowing application of gases to the nose and/or mouth of a person, comprising a gas delivery nozzle, a mask for covering the nose and mouth of the person, and a retaining strap means, characterised in that all parts of the mask assembly are integrally moulded of the same substantially non-elastic plastics material, the retaining strap means comprises a strap having a free end selectively connectable to the mask via a clip means in such a manner that the strap means is adjustable in length.

For the first time the invention provides a mask assembly the whole of which can be moulded in a single operation from a single plastics material which is usually flexible, but not very elastic and there is no requirement for separate insertion or attachment of strap means to hold the mask in place. The moulding of the mask assembly may thereby be carried out fully automatically by simply moulding the mask, for example, by injection moulding, in a single operation.

Preferred arrangements of the invention will now be described by way of example only and with reference to the accompanying drawings in which:

BRIEF DESCRIPTION OF THE DRAWINGS

FIG. 5 is an end view of the mask assembly of FIG. 3, FIG. 6 is a section of a nozzle part of the mask assembly of FIG. 3, and, FIG. 7 is a perspective view of part of the clip means of the mask assembly of FIG. 3.

DESCRIPTION OF THE PREFERRED EMBODIMENT

Figure 1:
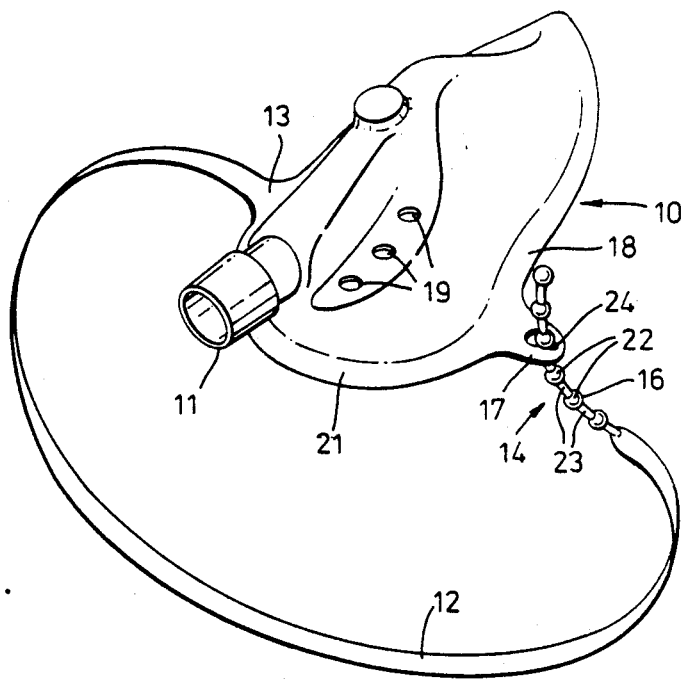
FIG. 1 is a perspective view of a first mask assembly according to the invention.

FIG. 1 illustrates a mask assembly comprising a one-piece injection moulding of plastics material (transparent, flexible, but substantially non-elastic polyvinyl chloride PVC moulded at 170°–180°). All of the parts illustrated are moulded of this plastic and no additional parts are necessary either during moulding (i.e. no separate metal clips etc are inserted in the mould before moulding) and no additional assembly work of clip parts or strap is necessary. The face mask assembly comprises a mask 10 incorporating a gas delivery nozzle 11, a strap 12 connected to one edge 13 of the mask 10, and a clip means 14 in two parts, one part 16 being formed at the free end of the strap 12 and the other part 17 being formed on an edge 18 of the face mask 10 opposite the edge 13 (although the part 17 could be formed on the free end of another strap attached to the mask). The mask 10 also includes exhaust apertures 19.

Although the mask assembly is injection moulded in one operation of the same PVC material, the thickness of the material and cross-section varies to allow the different parts of the face mask assembly to carry out their normal function. Thus for example the face mask 10 is generally of relatively thin material (typically 1.1 mm) with a flexible thin sealing edge seal 21 surrounding the mask 10 for sealing engagement with the face of the patient.

The cylindrical gas delivery nozzle 11 is formed of a predetermined standard dimension so as to fit with standard products such as nebulizers or venturis (typically 22 mm outer diameter) with predetermined tapers to accord with international standards. The nozzle is arranged so as to direct the gas flow through the nozzle 11 towards the nose of the person wearing the mask 10.

The cross-section and width of the strap 12 is chosen so as to provide sufficient strength for the strap. To provide a variation in the length of the strap in use, the clip portion 16 comprises, at the end of the strap 12, a plurality of spaced male parts in the form of spheres 22 linked by links 23. The other part 17 of the clip forming the female part comprises a keyhole shaped slot 24 with which the spheres 22 and links 23 engage.

Thus the effective length of the strap 12 (which is flexible but not elastic and therefore cannot be stretched to a desired length) can be adjusted by selecting the particular sphere/link combination to be engaged with the slot 24.

Figure 2:
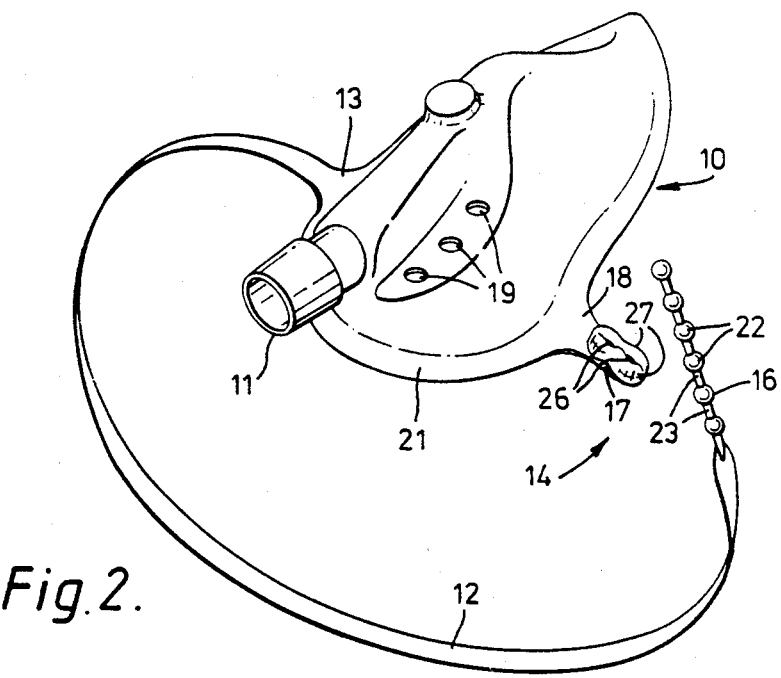
FIG. 2 is a perspective view of a second mask assembly incorporating a second embodiment of the invention.

FIG. 2 illustrates an alternative arrangement of face mask assembly. The parts of FIG. 2 are the same as in FIG. 1 except for the clip 14. The male part 16 of the clip is the same as in FIG. 1 but the female part, instead of being a keyhole shaped slot comprises a pair of sockets 26 part spherical with which two adjacent spheres 22 may engage. The sockets 26 are formed in resilient wall portions 27 which flex to allow insertion of the spheres into the sockets 26 and the flexible wall portions 27 then flex back to their normal position to clamp the spheres 22 in the sockets 26.

FIGS. 3 to 7 show a third embodiment of the invention. The same reference numerals are used as with respect to FIGS. 1 and 2 for similar parts.

The mask assembly is again a single one piece injection moulding of transparent flexible, but substantially non elastic polyvinyl chloride (PVC) which is moulded at a temperature of 170° to 180°. The injection point for the injection of the plastic during the moulding is indicated at 50 in substantially the middle of the front face of the mask 10. The wall thickness of the mask 10 is, as before, approximately 1.1 mm except for the cross shaped region 51 delineated by dotted lines. Within this region 51 the thickness of the wall of the mask 10 is increased to substantially double that thickness, approximately 2 mm. The thickened region 51 helps the mask 10 to maintain its shape and also allows, during moulding, plastic to more readily flow from the injection point 50 to other parts of the mould, and in particular the parts of the mould which form the strap means and the nozzle 11.

Figure 3:
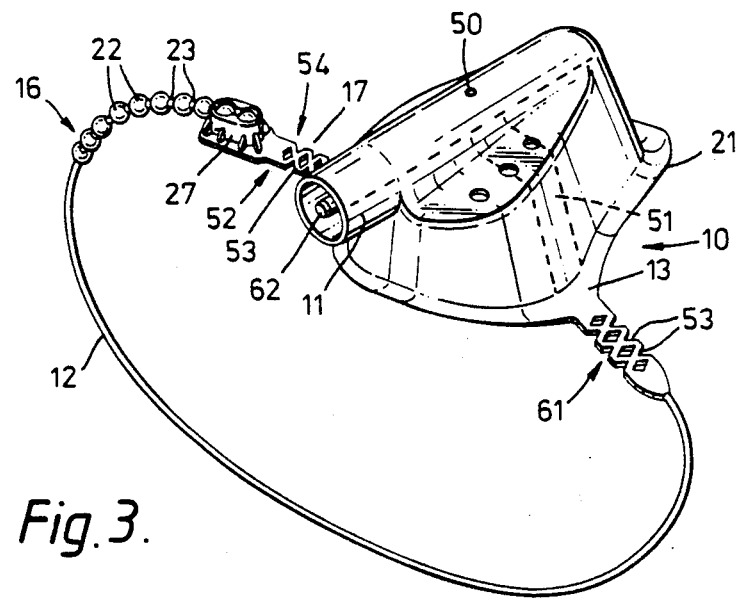
FIG. 3 is a perspective view of a third mask assembly incorporating a third embodiment of the invention.
Figure 4:
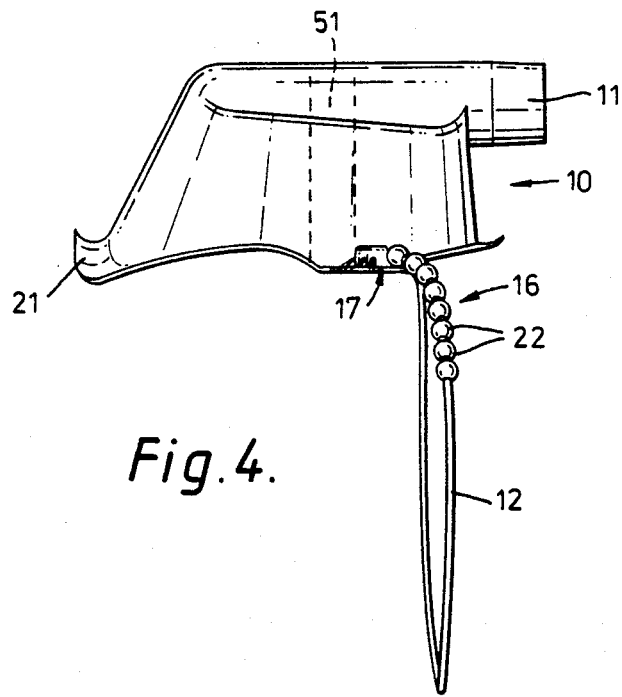
FIG. 4 is a side view of the mask assembly FIG. 3.

The mask 10 of the mask assembly of FIG. 3 is a somewhat different shape to that of FIGS. 1 and 2, as will be clear from the drawings.

Furthermore, in this case the female part 17 of the clip means is attached to the mask 10 by means of a short length of strap 52. The form of the strap 52 is clear from the drawing and comprises a succession of transverse links 53. The transverse links 53 form a series of "X's" the ends of the links of which are joined together. Thus, although the material form which the mask assembly is manufactured is substantially non-elastic, the strap 52 is flexible and thereby forms an elasticated section 54 which can be resiliently expanded in length. This expansion takes place by bending of the transverse links 53 with respect to each other from the straight line form shown in the drawing to a curved form whereby the length of the strap 52 can be resiliently increased.

Attached to the free end of this elasticated section 54 is the female clip part 17, the form of which is illustrated in the perspective view of FIG. 7 and which is similar to the female part of the clip shown in FIG. 2. It comprises two upstanding wall portions 27 each of which includes inwardly facing part spherical sockets 26. The wall portions 27 are connected to a base 59 in such a manner as to be slightly flexible away from one another.

The strap 12 is connected, as with the arrangements of FIGS. 1 and 2, to one edge 13 of the mask 10, except that in this case it is connected by means of an elasticated section 61 similar to the elasticated section 54. Furthermore, the strap 12 is of circular cross section and includes at its free end, as before, a male part 16 in the form of spheres 22 linked by links 23.

We will now describe the particular form of the nozzle 11 in this case. The nozzle is arranged so as to be connectable to a multiplicity of different types of connectors. Thus, as described with regard to FIGS. 1 and 2, the outer diameter of the outer most wall of the nozzle 22 mm. In addition, there is provided a central axis inner nozzle 62 having a standard outer diameter of 5.5 mm and a chamfered free end 63 adapted to be connected with oxygen supply tubes. The inner nozzle 62 is connected to the outer wall of the nozzle 11 by means of radial fingers 64 disposed at the inner end of the nozzle 11.

The edge 21 of the face mask which engages the face of the patient wearing the mask is flexible so as to substantially seal with the patient's face. This can cause problems particularly as, during prolonged use, water tends to be trapped between this edge 21 and the skin of the patient's face. Accordingly, in the mask of FIG. 3 (and the same technique can be applied to FIGS. 1 and 2) the part of the mould from which the surface of the edge 21 is moulded and hence the surface of the edge 21 is to be slightly rough. This prevents the close sealing of that surface with the patient's face and thereby prevent the trapping of liquid between that surface and the face and/or to allow the release of any liquids so trapped. This surface roughening of the part of the mould can be carried out in a number of ways, but the preferred method is to blast the surface with sand particles in a flow of gas, typically air (so called "vapour blasting").

The invention is not restricted to the details of the foregoing examples. For example the shape and disposition of the links in the elasticated sections 54,61. This "X's" may be replaced by, for example, "O's" opening squares, "S's" or other shapes.

I claim:

1. A mask assembly for allowing application of gases to the nose and mouth of a person, said mask assembly comprising a gas delivery nozzle, a mask adapted to cover the nose and mouth of the person, and a retaining strap means, the gas nozzle having one end connected to the mask and a free end adapted for connection to a connector assembly, the retaining strap means comprising clip means and a strap, the strap being adapted to extend around the back of the head of the person and having one end connected to one side of the mask and a free end, the clip means comprising first and second parts, one of said parts being attached to the free end of the strap and the other one of said parts being attached to the other side of the mask, a specified one of the first and second parts having first and second longitudinally spaced opposite ends, being attached to said mask or strap, respectively, at said first end and having means for connecting the other of said parts thereto at different selected positions along its length, so that the effective length of the strap means is variable, all parts of the mask assembly being integrally injection molded of the same substantially non-elastic plastics material.

2. A mask assembly as claimed in claim 1 characterized in that the free end of the gas delivery nozzle comprises an external nozzle part and an internal nozzle part, said external nozzle part comprising a substantially tubular portion having a predetermined outer circumferential size and configuration and said internal nozzle part comprising a substantially tubular portion having a predetermined outer circumferential size and configuration smaller than the outer circumferential size and configuration of said external nozzle part and said internal nozzle part being connected internally to and coaxially aligned with said external nozzle part whereby the gas delivery nozzle is connectable by means of a selected one of said external and internal nozzle parts to different types of connector assemblies.

3. A mask assembly as claimed in claim 1 characterized in that the gas delivery nozzle is arranged so as, in use, the axis of the delivery nozzle points to the nose of the person wearing the mask assembly.

4. A mask assembly as claimed in claim 1 characterized in that the strap means includes at least one elasticated part formed so that the strap means is expandable.

5. A mask assembly as claimed in claim 4 characterized in that said at least one elasticated part comprises a plurality of serially connected and aligned links, each of said links having a center point whereby said links are positioned so that a line through said center point extends transversely to the longitudinal axis of the strap means whereby said part may flex to provide the required expansion.

6. A mask assembly as claimed in claim 1 in which the mask has an edge portion adapted to abut the face of the person, characterized in that said edge portion is formed with a rough surface to prevent the trapping of fluid between the mask and the face and/or to allow the release of any liquid so trapped.

7. A mask assembly as claimed in claim 1 characterized in that one of said first and second parts of said clip means includes at least one female engaging portion and the other of said first and second parts includes at least one male engaging portion whereby the part which forms said specified part includes more than one engaging portion, said more than one engaging portions of said specified part comprising said means for connection.

8. A mask assembly as claimed in claim 7 wherein said part other than said specified part includes more than one engaging portion.

* * * * *